(12) United States Patent
Glauder et al.

(10) Patent No.: US 6,663,875 B2
(45) Date of Patent: Dec. 16, 2003

(54) HAIR PREPARATION FOR THE TREATMENT OF DANDRUFF

(75) Inventors: Jan Glauder, Frankfurt (DE); Roman Morschhaeuser, Mainz (DE); Angelika Turowski-Wanke, Kelkheim (DE); Waltraud Simsch, Kelkheim (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/219,865

(22) Filed: Aug. 15, 2002

(65) Prior Publication Data

US 2003/0044375 A1 Mar. 6, 2003

Related U.S. Application Data

(62) Division of application No. 09/637,540, filed on Aug. 11, 2000, now abandoned.

(30) Foreign Application Priority Data

Aug. 13, 1999 (DE) .......................... 199 38 404

(51) Int. Cl.⁷ .............................. A61K 7/06; A61K 7/00
(52) U.S. Cl. ...................... 424/401; 424/400; 424/70.1; 514/852
(58) Field of Search ................................. 424/400, 401, 424/70.1; 514/852

(56) References Cited

U.S. PATENT DOCUMENTS

| 4,741,855 A | 5/1988 | Grote et al. |
| 5,648,389 A | 7/1997 | Gans et al. .................. 514/557 |

FOREIGN PATENT DOCUMENTS

| DE | 2 024 051 | 12/1971 |
| GB | 1 333 475 | 10/1973 |
| WO | WO 96/29045 | 9/1996 |

OTHER PUBLICATIONS

Mixich, Von G., et al., "Ein Beitrag zur stereospezifischen Syntheses von antimykotisch wirksamen imidazolyloximathern", Arzneim.–Forsch / Drug Res. 29 (II), Nr. 10 (1979), pp. 1510–1513.

*Primary Examiner*—Shelley A. Dodson
(74) *Attorney, Agent, or Firm*—Richard P. Silverman

(57) ABSTRACT

Cosmetic preparations, in particular shampoos, are described which comprise oxiconazole nitrate as antidandruff agent.

9 Claims, No Drawings

HAIR PREPARATION FOR THE TREATMENT OF DANDRUFF

CROSS-REFERENCE TO RELATED APPLICATION

This application is a Division of copending application Ser. No. 09/637,540 filed Aug. 11, 2000 now abandoned, the contents of which is hereby incorporated by reference.

BACKGROUND OF THE INVENTION

The present invention relates to cosmetic preparations, in particular antidandruff compositions and deodorizing cosmetic compositions, comprising Z-1-(2,4-dichlorophenyl)-2-(1H-imidazol-1-yl)-O-(2,4-dichlorobenzyl)ethanone oxime or salts thereof from inorganic and organic acids, in, particular Z-1-(2,4-dichlorophenyl)-2-(1H-imidazol-1-yl)-O-(2,4-dichlorobenzyl)ethanone oxime nitrate (oxiconazole nitrate).

The fungicidal effectiveness of Z-1-(2,4-dichlorophenyl)-2-(1H-imidazol-1-yl)-O-(2,4-dichlorobenzyl)ethanone oxime nitrate (oxiconazole nitrate) is, as described in the publication Arzneim.-Forsch./Drug Res. 29 (II), No.10 (1979), p. 1510 ff, known.

The use of oxiconazole nitrate in broad-spectrum antimycotics for the curative treatment of dermatological disorders is described in U.S. Pat. No. 5,648,389. The compositions described therein for the treatment of acne comprise, in addition to an antimicrobial active ingredient, one or more hydroxy acid(s) and a water-soluble zinc compound.

WO 96/29045 proposes compositions for the treatment of scalp dermatitis consisting of a combination of cytotoxic agents, for example zinc pyrithione or selenium sulfide and a fungicide, for example oxiconazole.

It has now been found that Z-1-(2,4-dichlorophenyl)-2-(1H-imidazol-1-yl)-O-(2,4-dichlorobenzyl)ethanone oxime and salts thereof, in particular the nitrate, can be used as antidandruff agents in cosmetic preparations.

SUMMARY OF THE INVENTION

Surprisingly it has been found that said cosmetic preparations can be free of other active substances. In particular they can be free of cytotoxic agents like zinc pyrithione or selenium sulfide.

The invention provides cosmetic preparations comprising Z-1-(2,4-dichlorophenyl)-2-(1H-imidazol-1-yl)-O-(2,4-dichlorobenzyl)ethanone oxime or salts thereof. In this connection, suitable salts are, preferably, the nitrate, chloride, bromide, perchlorate or acetate. Particular preference is given to the nitrate.

The Z-1-(2,4-dichlorophenyl)-2-(1H-imidazol-1-yl)-O-(2,4-dichlorobenzyl)-ethanone oxime and salts thereof to be used in the cosmetic preparations can, for example be prepared by a process as described in the publication Arzneim.-Forsch./Drug Res. 29 (II), No.10 (1979), p. 1510 ff.

In particular the invention relates to cosmetic preparations which are free of cytotoxic agents like zinc pyrithione or selenium sulfide.

For the use according to the invention of said compounds, a very wide variety of cosmetic preparations are suitable, in particular shampoos. Examples of further preparations which are suitable in accordance with the invention and which may be mentioned are the following hair care and styling compositions: hair rinses, hair treatments, hair regenerators, hair lotions, water-wave lotions, hair sprays, styling creams, styling gels, hair oils, hair pomades or hair brilliantines. Accordingly, these are all preparations which, depending on their actual intended use, are applied to the hair and the scalp for a shorter or longer period. By adding the compounds according to the invention, the dandruff treatment is effected.

The shampoos can be a clear liquid, opaque liquid (with a pearlescent effect), creamy or gel-like.

The washing raw materials which form the basis of these shampoos can be of an ionic, cationic, nonionic and amphoteric nature, and also be present in combinations of these substances. The total amount of surfactants used in the compositions according to the invention can be between 5% by weight and 70% by weight, preferably between 10% by weight and 40% by weight, particularly preferably between 12% by weight and 35% by weight, based on the finished composition.

Examples of anionic detersive substances of this type which may be mentioned are:

$C_{10}$–$C_{20}$-alkyl- and -alkylenecarboxylates, alkyl ether carboxylates, fatty alcohol sulfates, fatty alcohol ether sulfates, alkylolamide sulfates and sulfonates, fatty acid alkylolamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein-fatty acid condensation products, alkyl monoglyceride sulfates and sulfonates, alkyl glyceride ether sulfonates, fatty acid methyltaurides, fatty acid sarcosinates and sulforicinoleates. These compounds and mixtures thereof are used in the form of their water-soluble or water-dispersible salts, for example the sodium, potassium, magnesium, ammonium, mono-, di- and triethanolammonium and analogous alkylammonium salts.

The proportion by weight of the anionic surfactants in the compositions according to the invention is in the range from 7% to 30%, preferably 10% to 25%, particularly preferably 12% to 22%.

Suitable cationic surfactants are, for example, quaternary ammonium salts, such as di($C_{10}$–$C_{24}$-alkyl)dimethylammonium chloride or bromide, preferably di($C_{12}$–$C_{18}$-alkyl)dimethylammonium chloride or bromide; $C_{10}$–$C_{24}$-alkyldimethylethylammonium chloride or bromide; $C_{10}$–$C_{24}$-alkyl-trimethylammonium chloride or bromide, preferably cetyltrimethyl-ammonium chloride or bromide and $C_{20}$–$C_{22}$-alkyltrimethylammonium chloride or bromide; $C_{10}$–$C_{24}$-alkyldimethylbenzylammonium chloride or bromide, preferably $C_{12}$–$C_{18}$-alkyldimethylbenzylammonium chloride; N—($C_{10\text{-}C18}$-alkyl)-pyridinium chloride or bromide, preferably N—($C_{12}$–$C_{16}$-alkyl)pyridinium chloride or bromide; N—($C_{10}$–$C_{18}$-alkyl)isoquinolinium chloride, bromide or monoalkyl sulfate; N—($C_{12}$–$C_{18}$-alkyloylcolaminoformylmethyl)pyridinium chloride; N—($C_{12}$–$C_{18}$-alkyl)-N-methylmorpholinium chloride, bromide or monoalkyl sulfate; N—($C_{12}$–$C_{18}$-alkyl)-N-ethylmorpholinium chloride, bromide or monoalkyl sulfate; $C^{16}$–$C^{18}$-alkyl-pentaoxethylammonium chloride; diisobutylphenoxyethoxyethyl-dimethyl-benzylammonium chloride; distearoylethylhydroxyethylmonium methosulfate; dicocoylethylhydroxyethylmonium methosulfate; salts of N,N-diethylamino-ethylstearylamide and -oleylamide with hydrochloric acid, acetic acid, lactic acid, citric acid, phosphoric acid; N-acylamidoethyl-N,N-diethyl-N- methylammonium chloride, bromide or monoalkyl sulfate and N-acylaminoethyl-N,N-diethyl-N-benzylammonium chloride, bromide or monoalkyl sulfate, where acyl is preferably stearyl or oleyl.

The proportion by weight of the cationic surfactants in the compositions according to the invention is in the range from 0.05% to 10%, preferably 0.05% to 5%, particularly preferably 0.1% to 3%.

Suitable nonionic surfactants which can be used as detersive substances are, for example: fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); alkyl polyglycosides, N-alkyl-, N-alkoxypolyhydroxy fatty acid amide, in particular N-methyl-fatty acid glucamide, sucrose esters; sorbitol esters,and esters of sorbitol polyglycol ethers.

The proportion by weight of nonionic surfactants in the compositions according to the invention is in the range from 1 to 20%, preferably 2 to 10%, particularly preferably 3 to 7%.

Examples of suitable amphoteric surfactants are: lauro- and coco-amphoacetates, N—($C_{12}$–$C_{18}$-alkyl)-β-aminopropionates and N—($C_{12}$–$C_{18}$-alkyl)-β-iminodipropionates as alkali metal and mono-, di- and trialkylammonium salts; N-acylamidoalkyl-N,N-dimethylacetobetaine, preferably N—($C_8$–$C_{18}$-acyl) amidopropyl-N,N-dimethylaceto-betaine; $C_{12}$–$C_{18}$-alkyldimethylsulfopropylbetaine; amphoteric surfactants based on imidazoline (commercial name: Miranol®, Steinapon®), preferably the sodium salt of 1-(β-carboxymethyloxyethyl)-1-(carboxymethyl)-2-lauryl-imidazolinium; amine oxide, e.g. $C_{12}$–$C_{18}$-alkyldimethylamine oxide, fatty acid amidoalkyldimethylamine oxide.

The proportion by weight of amphoteric surfactants in the compositions according to the invention is in the range from 0.5 to 20%, preferably 1 to 10%. Furthermore, foam-intensifying cosurfactants from the group of alkylbetaines, alkylamidobetaines, aminopropionates, aminoglycinates, imidazoliniumbetaines and sulfobetaines, amine oxides and fatty acid alkanolamides or polyhydroxyamides can be used in the compositions according to the invention.

Preferred surfactants in the compositions according to the invention are lauryl sulfate, laureth sulfate, cocoamidopropylbetaine, sodium cocoyl glutamate, sodium lauryl glutamate, disodium laureth sulfosuccinate and coconut fatty acid diethanolamide.

The preparations according to the invention can additionally comprise further additives customary in cosmetics, for example emulsifiers, coemulsifiers, superfatting agents, fats, oils, waxes, stabilizers, biogenic active ingredients, glycerol, preservatives, pearlizing agents, opacifiers, pigments, colorants and fragrances, solvents, thickeners and dispersants, and also protein derivatives, such as gelatin, collagen hydrolyzates, natural- and synthetic-based polypeptides, egg yolk, lecithin, lanolin and lanolin derivatives, fatty alcohols, silicones, deodorizing agents, substances having keratolytic and keratoplastic action, enzymes and carrier substances. Furthermore, further antimicrobially effective agents can be added to the compositions according to the invention.

Examples of emulsifiers which can be used are: sorbitan esters, sorbitol esters, phosphoric esters, monoglycerides, polysorbates, polyethylene glycol mono/di-fafty acid esters, fatty acids with a high degree of ethoxylation, and high molecular weight silicone compounds, such as, for example, dimethylpolysiloxanes having an average molecular weight of from 10,000 to 50,000.

Suitable nonionic O/W coemulsifiers are addition products of 2 to 30 mol of ethylene oxide and/or 0 to 5 mol of propylene oxide with linear fatty alcohols having 8 to 22 carbon atoms, with fatty acids having 12 to 22 carbon atoms and with alkylphenols having 8 to 15 carbon atoms in the alkyl group; $C_{12}$–$C_{18}$-fatty acid mono- and diesters of addition products of 1 to 30 mol of ethylene oxide with glycerol, glycerol mono- and diesters and sorbitan/sorbitol mono- and diesters of saturated and unsaturated fatty acids having 6 to 22 carbon atoms and ethylene oxide addition products thereof; addition products of 15 to 60 mol of ethylene oxide with castor oil and/or hydrogenated castor oil, polyol and, in particular, polyglycerol esters, such as, for example, polyglycerol polyricinoleate and polyglycerol poly-12-hydroxystearate. Likewise suitable are mixtures of compounds from two or more of these classes of substances. The addition products of ethylene oxide and/or propylene oxide with fatty alcohols, fatty acids, alkylphenols, glycerol mono- and diesters, and sorbitan mono- and diesters of sorbitol mono- and diesters of fatty acids or with castor oil are known, commercially available products. These are homolog mixtures whose average degree of alkoxylation corresponds to the ratio of the amounts of ethylene oxide and/or propylene oxide and substrate with which the addition reaction is carried out. $C_{12}$–$C_{18}$-Fatty acid mono- and diesters of addition products of ethylene oxide with glycerol are known from DE 20 24 051 as refatting agents for cosmetic preparations.

Superfatting agents which can be used are substances such as, for example, polyethoxylated lanolin derivatives, lecithin derivatives, polyol fatty acid esters, monoglycerides and fatty acid alkanolamides, the latter also serving as foam stabilizers. Typical examples of fats are glycerides, and suitable waxes are inter alia beeswax, paraffin wax or microcrystalline waxes, optionally in combination with hydrophilic waxes, e.g. cetystearyl alcohol.

Stabilizers which can be used are metal salts of fatty acids, such as, for example, magnesium, aluminum and/or zinc stearate.

The term biogenic active ingredients means, for example, plant extracts and vitamin complexes.

Suitable preservatives are, for example, phenoxyethanol, formaldehyde solution, parabens, pentanediol or sorbic acid. Suitable pearlizing agents are, for example, glycol stearic esters, such as ethylene glycol distearate, but also fatty acid monoglycol esters.

Colorants which can be used are the substances approved and suitable for cosmetic purposes, as listed, for example, in the publication "Kosmetische Färbemittel" [Cosmetic Coloring agents] from the Farbstoffkommission der Deutschen Forschungsgemeinschaft [Colorants Commission of the German Research Council], Verlag Chemie, Weinheim, 1984, pp. 81–106.

Suitable thickeners are sodium, potassium, ammonium chloride, sodium sulfate, fatty acid alkylolamides, cellulose derivatives, for example hydroxyethylcellulose, guar gum, polyvinyl alcohol, polyvinylpyrrolidone, hydroxypropyl guar gum, starch and starch derivatives, and natural gums, carboxylvinyl polymers, for example Carbopol 934, 940, 941, 956, 980, 981, 1342 and 1382.

The thickeners and dispersants used are acyl derivatives and amine oxides having long-chain aliphatic groups having 8–22, preferably 14–22, particularly preferably 16–22, carbon atoms and mixtures thereof, and also long-chain ethylene glycol esters, alkanolamides, long-chain fatty acid esters, glycerol esters, alkanolamide esters and alkyldimethylamine oxides, and the dispersants mentioned in U.S. Pat. No. 4,741,855.

Particularly suitable for shampoos are ethylene glycol esters of fatty acids having 14 to 22, particularly preferably, 16 to 22, carbon atoms, in particular mono- and diethylene glycol stearate. Preference is also given to stearin monoethanolamide, stearin diethanolamide, stearin isopropanolamide, stearin monoethanolamide stearate, stearyl stearate, cetyl palmitate, glyceryl stearate, stearamide diethanolamide distearate, stearamide monoethanolamide stearate, N,N-dihydrocarbyl (C12–C22, in particular C16–C18)-amidobenzoic acid and soluble salts thereof, N,N-di(C16–C18)-amidobenzoic acid and derivatives.

The dispersants are used in concentrations of from 0.5 to 10% by weight, preferably from 0.5 to 5% by weight, particularly preferably from 1 to 4% by weight, based on the finished composition.

Suitable carrier materials are vegetable oils, natural and hydrogenated oils, waxes, fats, water, alcohols, polyols, glycerol, glycerides, liquid paraffins, liquid fatty alcohols, sterol, polyethylene glycols, cellulose and cellulose derivatives.

In order to improve the affinity of Z-1-(2,4-dichlorophenyl)-2-(1H-imidazol-1-yl)-O-(2,4-dichlorobenzyl)ethanone oxime used according to the invention, or salts thereof on the skin or scalp, it is possible to use cationic guar polymers in weight amounts of from 0.01 to 5.0%, preferably 0.02 to 1.0%, as described in WO 97/26854. The effect of the active ingredient used according to the invention can be improved by adding polyethylene glycol (PEG), in particular having 6 to 22 EO groups, preferably PEG-12, polypropylene glycol (PPG), polyethoxy/polypropoxy copolymers, polyethyleneimines, polyethoxylated polyethyleneimines, polyethylene oxide fatty acid glycerides, ethoxylated nonylphenol, ethoxylated alcohols, polyethylene carbohydrates. Silicones, polyalkylsiloxanes, polyalkylarylsiloxanes, polyethersiloxane copolymers, as described in U.S. Pat. No. 5,104,645 and publications cited therein, improve the care action of the compositions according to the invention. The preparations according to the invention are prepared in a manner known per se by mixing the individual components and, if necessary, further processing them in a manner appropriate for the respective type of preparation. Some of these diverse possible preparation forms are described by way of example in the working examples.

Examples of other hair cosmetic preparations in which Z-1-(2,4-dichlorophenyl)-2-(1H-imidazol-1-yl)-O-(2,4-dichlorobenzyl) ethanone oxime or salts thereof can be used according to the invention and which may be mentioned are: hair rinses, hair treatments and hair regenerating compositions, which are rinsed out of the hair after a certain time or, depending on the formulation, can also remain on the hair. These preparations comprise inter alia substances from the group of the abovementioned cationic surfactants, which display a reviving and antistatic property on the hair.

The preparations according to the invention can also be presented in the form of aqueous and aqueous-alcoholic hair lotions, water-wave lotions (hair setting compositions), including those in gel form, and in aerosol form as hair spray, and in the form of hair care and styling creams and gels. The alcohols used are preferably ethanol and isopropanol.

Examples of resins having a hair-setting and style-holding action, which may be present in a concentration of from 0.5 to 6% by weight, preferably 1 to 3% by weight, in the corresponding preparations (hair setting compositions, hair spray) are: shellac and derivatives, reaction products of rosin with acrylic acid, poly-N-vinylpyrrolidone and alkyl-substituted poly-N-vinylpyrrolidone, poly-N-vinyl-N-alkylacetamide, polyvinyl acetate and partially hydrolyzed polyvinyl acetate, polyvinyl alcohol, alkyl esters of acrylic acid, mixed polymers of vinyl acetate and N-vinyl-N-alkylacetamide, mixed polymers of vinyl acetate and N-vinylpyrrolidone, reaction products of mixed polymers of vinyl acetate and acrylic acid or crotonic acid with organic bases, mixed polymers of vinyl acetate and maleic monoester, mixed polymers of vinyl acetate, vinyl pivalate and crotonic acid, mixed polymers of fatty acid vinyl esters and (meth)acrylic acid, mixed polymers of (meth)acrylic esters and N-vinylpyrrolidone, mixed polymers of acrylic esters and (meth)acrylic acid, alkyl esters of mixed polymers of methyl vinyl ether and maleic anhydride, alkyl esters of mixed polymers of olefins and maleic anhydride, polyvinylacetals and polyvinylbutyrals, dimethylhydantoin-formaldehyde condensates, cyclohexanone-formaldehyde resins, phthalate resins, protein hydrolyzates and protein derivatives, starch derivatives and cellulose derivatives, which may also contain cationic groups, and further film formers containing quaternary groups, such as reaction products of mixed polymers of alkyl (meth)acrylates and dimethylaminoethyl (meth)acrylate with alkylating agents, and also quaternary copolymers of N-vinylpyrrolidone and dialkylaminoalkyl (meth)acrylates.

All of these preparations are also prepared—as already mentioned in the case of the shampoo—in a manner known per se, with the addition of the active ingredient used according to the invention.

The antidandruff active ingredient is incorporated into the preparations according to the invention in amounts customarily between about 0.05 and about 10% by weight, based,on the total preparation. Within this range, the concentrations of the specific preparations depend on their intended use. Certain preparation forms such as, for example, concentrates, which are diluted prior to use, can also have considerably higher concentrations.

For preparations which remain on the hair, such as, for example, hair lotions, hair setting compositions, creams etc., lower concentrations are used, for example of from about 0.01 to about 1% by weight, preferably 0.1 to 0.5% by weight. They are expediently used in higher concentrations for cosmetic preparations which, optionally after dilution, act on hair and scalp for only a short period, such as, for example, shampoos or hair rinses. In these cases, concentrations of from about 0.2 to about 10% by weight, preferably from about 0.5 to about 2% by weight, for example, can be expedient.

The use according to the invention of said Z-1-(2,4-dichlorophenyl)-2-(1H-imidazol-1-yl)-O-(2,4-dichlorobenzyl) ethanone oxime and salts thereof, in particular oxiconazole nitrate, has numerous advantages over the prior art mentioned.

The main advantages are:
low use concentrations
broad antimicrobial activity spectrum
low toxicity.

Oxiconazole nitrate, which is preferably used, is used either in dissolved form, or as a white powder, the particle size preferably being between 50 nm and 1000 nm. Suitable solvents are, for example, ethanol, acetone, n-octanol, polyethylene glycol 400, propylene glycol, butylene glycol, glycerol.

The examples below illustrate the present invention. The stated amounts are based on weight.

EXAMPLES

Example 1

Cream Shampoo

| | | |
|---|---|---|
| Oxiconazole nitrate | | 1.5% |
| Fatty acid methyltauride sodium salt | | 70% |
| (® Hostapon CT-Paste, Clariant GmbH) | | |
| Fatty acid methylisethionate sodium salt | | 5% |
| (® Hostapon SCI-65 Clariant GmbH) | | |
| Palm kernel fatty acid sarcoside (® Medialan LD) | | 5% |
| Ethyleneglycol distearate | | 1.50% |
| Water | ad | 100% |

Example 2

Antidandruff Shampoo

| | | |
|---|---|---|
| Oxiconazole nitrate | | 0.8% |
| Fatty acid monoethanolamide polyglycol ether | | 5% |
| (® Genagen CA-050, Clariant GmbH) | | |
| Alkyl ether sulfate sodium salt | | 35.0% |
| (® Genapol LRO liq., Clariant GmbH) | | |
| Acylaminopolyglycol ether sulfat magnesium salt | | 10.0% |
| (® Genapol AMG, Clariant GmbH) | | |
| Alkylamidopropylbetaine | | 8.0% |
| (® Genagen CAB, Clariant GmbH) | | |
| Bodying agent | | 2.0% |
| (® Genapol L-3, Clariant GmbH) | | |
| Sodium chloride | | 0.7% |
| Water | ad | 100% |

Example 3

Antidandruff Shampoo

| | | |
|---|---|---|
| Ammonium lauryl sulfate | | 5.00% |
| Alkyl ether sulfate sodium salt | | 15.00% |
| (® Genapol LRO Paste, Clariant GmbH) | | |
| Sodium lauroylsarcosinate | | 1.50% |
| Ethylene glycol distearate | | 1.50% |
| Genapol PGL, Clariant GmbH | | |
| Oxiconazole nitrate | | 3.00% |
| Water | ad | 100% |

Example 4

3 in 1 Shampoo

| | | |
|---|---|---|
| Oxiconazole nitrate | | 0.6% |
| Alkyl ether sulfate sodium salt | | 35.0% |
| (® Genapol LRO. liq., Clariant GmbH) | | |
| Acylaminopolyglycol ether sulfate magnesium salt | | 5.0% |
| (® Genapol AMG, Clariant GmbH) | | |

-continued

| | | |
|---|---|---|
| Fatty acid glutamate sodium salt | | 5.0% |
| (® Hostapon KCG, Clariant GmbH) | | |
| Fatty acid-protein condensate | | 5.0% |
| (® Hostapon SCHC, Clariant GmbH) | | |
| Silicone oil | | 2.0% |
| (® Belsil DNC 6032, Wacker Chemie) | | |
| D-Panthenol | | 1.0% |
| Bodying agent | | 2.5% |
| (® Genapol L-3, Clariant GmbH) | | |
| Alkylamidopropylbetaine | | 8.0% |
| (® Genagen CAB, Clariant GmbH) | | |
| Sodium chloride | | 2.0% |
| Water | ad | 100% |

Example 5

Shampoo Concentrate

| | | |
|---|---|---|
| Oxiconazole nitrate | | 1.5% |
| Alkyl ether sulfate sodium salt | | 20.0% |
| (® Genapol LRO Paste, Clariant GmbH) | | |
| Alkylamidopropylbetaine | | 33.0% |
| (® Genapol CAB, Clariant GmbH) | | |
| Fatty acid monoethanolamide polyglycol ether | | 5.0% |
| (® Genagen CA-050, Clariant GmbH) | | |
| Fatty acid-protein condensate | | 5.5% |
| (® Hostapon SCHCP, Clariant GmbH) | | |
| Bodying agent | | 3.0% |
| (® Genapol L-3, Clariant GmbH) | | |
| Water | ad | 100% |

Example 6

Liquid Soap

| | | |
|---|---|---|
| Oxiconazole nitrate | | 0.1% |
| Alkyl ether sulfate sodium salt | | 40.0% |
| (® Genapol LRO, Clariant GmbH) | | |
| sec. n-Alkylsulfonate sodium salt | | 8.0% |
| (® Hostapur SAS, Clariant GmbH) | | |
| Bodying agent | | 3.0% |
| (® Genapol L-3, Clariant GmbH) | | |
| Sodium chloride | | 1.5% |
| Water | ad | 100% |

Example 7

Deodorant Soap

| | |
|---|---|
| Oxiconazole nitrate | 1.0% |
| Basic soap | 99.0% |

Example 8

Roll-on Deodorant

| | |
|---|---|
| Oxiconazole nitrate | 0.1% |
| Hydroxyethyl cellulose ether | 0.7% |
| (® Tylose H 10000, Clariant GmbH) | |

-continued

| | |
|---|---|
| Ethanol | 40.0% |
| 1,2-Propylene glycol | 5.0% |
| Solubilizer | 0.5% |
| (® Cremophor RH 455, BASF AG) | |
| Water | 53.0% |

Example 9

Deodorant

| | | |
|---|---|---|
| Oxiconazole nitrate | | 0.15% |
| Ethanol | | 70.0% |
| Refatting agent | | 0.5% |
| (® Softigen 767, Chem. Werke Hüls) | | |
| Parfume oil | | 0.5% |
| Allantoin | | 0.1% |
| Water | ad | 100% |

Example 10

Hair After-rinse

| | | |
|---|---|---|
| Oxiconazole nitrate | | 1.2% |
| Cetyl alcohol | | 2.5% |
| Paraffin oil | | 1.5% |
| Phosphoric ester compound | | 1.5% |
| (® Hostaphat KL340N, Clariant GmbH) | | |
| Alkylpolyethoxyammonium lactate | | 7.0% |
| (® Genamin KSL, Clariant GmbH) | | |
| Hydroxyethyl cellulose ether | | 0.6% |
| (® Tylose, Clariant GmbH) | | |
| Water | ad | 100% |

Example 11

Hair Lotion

| | |
|---|---|
| Oxiconazole nitrate | 0.05% |
| Fatty acid polyglycol ether | 0.6% |
| (® Emulsogen EL, Clariant GmbH) | |
| Ethanol | 40.0% |
| Alkylpolyethoxyammonium lactate | 0.3% |
| (® Genamin KSL, Clariant GmbH) | |
| D-Panthenol | 0.5% |
| Water | ad 100% |

Example 12

Hair Setting Composition

| | |
|---|---|
| Oxiconazole nitrate | 0.1% |
| Isopropanol | 40.0% |
| Polyethylene glycol ($M_w$ = 400) | 0.5% |
| Alkylpolyethoxyammonium lactate | 0.7% |
| (® Genamin KSL, Clariant GmbH) | |
| Refatting agent | 0.6% |
| Polyvinylpyrrolidone | 5.5% |
| (® Luviskol, BASF AG) | |
| Water | ad 100% |

Example 13

Oil-in-water Cream

| | |
|---|---|
| Oxiconazole nitrate | 0.05% |
| 1,2-Propylene glycol | 10.0% |
| Oil-in-water emulsifier | 12.0% |
| (® Hostacerin CG, Clariant GmbH) | |
| Oil component | 8.0% |
| (® Entanol G, Henkel KG & A) | |
| Paraffin oil | 5.0% |
| Isopropyl isostearate | 5.0% |
| Bodying agent | 0.3% |
| (® Carbopol 940, Goodrich) | |
| Sodium hydroxide solution (10% strength) | 0.4% |
| Water | ad 100% |

What is claimed is:

1. A process for treating dandruff comprising contacting hair with a hair preparation which comprises an effective amount of Z-1-(2,4-dichlorophenyl)-2-(1H-imidazol-1-yl)-O-(2,4-dichlorobenzyl)ethanone oxime or salts thereof from inorganic and organic acids, said hair preparation being free of cytotoxic agents.

2. The process of claim 1 wherein the hair preparation comprises Z-1-(2,4-dichlorophenyl)-2-(1H-imidazol-1-yl)-O-(2,4-dichlorobenzyl)ethanone oxime nitrate.

3. The process of claim 1 wherein the hair preparation comprises a shampoo.

4. The process of claim 1 wherein the hair preparation is selected from the group consisting of shampoo, hair rinses, hair regenerators, hair lotions, water-wave lotions, styling creams, styling gels, hair oils, and hair pomades.

5. The process of claim 1 further comprising rinsing the hair reparation from the hair.

6. The process of claim 5 wherein the hair preparation comprises a shampoo.

7. The process of claim 5 wherein the hair preparation is selected from the group consisting of shampoo, hair rinses, hair regenerators, hair lotions, water-wave lotions, styling creams, styling gels, hair oils, and hair pomades.

8. A process for treating dandruff comprising contacting hair with a shampoo which comprises an effective amount of Z-1-(2,4-dichlorophenyl)-2-(1H-imidazol-1-yl)-O-(2,4-dichlorobenzyl)ethanone oxime nitrate, the shampoo being free of cytotoxic agents; and rinsing the shampoo from the hair.

9. A process for treating dandruff comprising contacting hair with a shampoo consisting essentially of an effective amount of oxiconazole nitrate, anionic surfactants, cationic surfactants, nonionic surfactants, amphoteric surfactants, emulsifiers, coemulsifiers, superfatting agents, fats, oils, waxes, stabilizers, biogenic active ingredients, glycerol, preservatives, pearlizing agents, opacifiers, pigments, colorants, fragrances, solvents, thickeners and dispersants, protein derivatives, fatty alcohols, silicones, deodorizing agents, substances having kerotolytic and keratoplastic action, enzymes, and carrier substances.

* * * * *